(12) United States Patent
Camussi et al.

(10) Patent No.: US 8,507,448 B2
(45) Date of Patent: Aug. 13, 2013

(54) HUMAN CD154-BINDING SYNTHETIC PEPTIDE AND USES THEREOF

(75) Inventors: Giovanni Camussi, Turin (IT); Ilaria Deambrosis, Turin (IT)

(73) Assignee: Fresenius Medical Care Deutschland G.m.b.H., Bad Homburg (DE)

( * ) Notice: Subject to any disclaimer, the term of this patent is extended or adjusted under 35 U.S.C. 154(b) by 331 days.

(21) Appl. No.: 12/734,908

(22) PCT Filed: Nov. 27, 2008

(86) PCT No.: PCT/EP2008/066349
§ 371 (c)(1),
(2), (4) Date: Jun. 2, 2010

(87) PCT Pub. No.: WO2009/071486
PCT Pub. Date: Jun. 11, 2009

(65) Prior Publication Data
US 2011/0144038 A1 Jun. 16, 2011

(30) Foreign Application Priority Data
Dec. 3, 2007 (EP) .................................... 07122164

(51) Int. Cl.
*A61K 38/04* (2006.01)
*A61K 38/08* (2006.01)
(52) U.S. Cl.
USPC ........................................ 514/21.7; 514/19.3
(58) Field of Classification Search
None
See application file for complete search history.

(56) References Cited

U.S. PATENT DOCUMENTS
2011/0065675 A1* 3/2011 Buchwald et al. ............ 514/150

FOREIGN PATENT DOCUMENTS
| WO | WO 01/95928 A2 | 12/2001 |
| WO | WO 02/18445 A2 | 3/2002 |
| WO | WO 02/18446 A2 | 3/2002 |
| WO | WO 2007/033058 A2 | 3/2007 |

OTHER PUBLICATIONS

Deambrosis et al ('Inhibition of CD40-CD154 costimulatory pathway by a cyclic peptide targeting CD154' J Mol Med (2009) 87:181-197).*
Minetake, K., et al., "Identification of three novel peptides that inhibit CD40-CD154 interation," Modern Rheumatology: Official Journal of the Japan College, vol. 15, No. 6, pp. 423-426, (Dec. 2005).
Foy, T.M., et al., "Immune regulation by CD40 and its ligand GP39," Annual Review of Immunology, Annual Reviews Inc., vol. 14, No. 1, pp. 591-617, (Jan. 2006).
Aoki-Ota, M., et al., "Tolerance induction by the blockade of CD40/CD154 international in pemphigus vulgaris mouse model," Journal of Investigative Dermatology, vol. 126, No. 1, pp. 105-113, (Jan. 2006).

Van Kooten, C., et al., "CD40-CD40 Ligand," Journal of Leukocyte Biology, vol. 67, pp. 2-17, (Jan. 2000).
Aruffo, A.M., et al., "The CD40 ligand, gp39, is defective in activated T cells from patients with x-linked hyper-IgM syndrome," Cell, vol. 72, pp. 291-300, (Jan. 1993).
Schonbeck, U., et al., "CD40 signaling and plaque instability," Circulation Research, vol. 89, pp. 1092-1103, (Dec. 2001).
Henn, V., et al., "CD40 ligand on activated platelets triggers an inflammatory reaction of endothelial cells," Nature, vol. 391, pp. 591-594 (Feb. 1998).
Biancone, L., et al., CD40-CD154 interaction in experimental and human disease (Review), International Journal of Molecular Medicine, vol. 3, pp. 343-353, (1999).
Buchner, K., et al., "CD40 ligand is selectively expressed on CD4+ T cells and platelets: implications for CD40-CD40L signalling in atherosclerosis," Journal of Pathology, vol. 201, pp. 288-295, (2003).
Bussolati, B., et al., "Expression of CD154 on renal cell carcinomas and effect on cell proliferation, motility and platelet-activating factor synthesis," Int. J. Cancer, vol. 100, pp. 654-661 (2002).
Biancone, L., et al., "Activation of CD40 favors the growth and vascularization of kaposi's sarcoma," Journal of Immunology, vol. 163, pp. 6201-6208, (1999).
Cantaluppi, V., et al., "The expression of CD154 by kaposi's sarcoma cells mediates the anti-apoptotic and migratory effects of HIV-1-TAT protein," Int. Journal of Immunopathology and Pharmcology, vol. 19, No. 1, pp. 81-96 (2006).
Hill, S.C., et al., "Activation of CD40 in cervical carcinoma cells facilitates CTL responses and augments chemotherapy-induced apoptosis," Journal of Immunology, vol. 174, pp. 41-50 (2005).
Melichar, B., et al., "Expression of CD40 and growth-inhibitory activity of CD40 ligand in ovarian cancer cell lines," Gynecologic Oncology, vol. 104, pp. 707-713, (2007).
Eliopoulos, A.G., et al., "The role of the CD40 pathway in the pathogenesis and treatment of cancer," Science Direct, Current Opinion in Pharmacology vol. 4, pp. 36-367, (2004).
Dicker, F., et al., "CD154 induces p73 to overcome the resistance to apoptosis of chronic lymphocytic leukemia cells lacking functional p53," Blood, vol. 108, No. 10, pp. 3450-3457, (Nov. 2006).
Boumpas, D.T., et al., "A short course of BG9588 (anti-CD40 ligand antibody) improves serologic activity and decreases hematuria in patients with proliferative lupus glomerulonephritis," Arthritis & Rheumatism, vol. 48, No. 3, pp. 719-727, (Mar. 2003).
Liossis, S.N., et al., "Costimulation blockade in the treatment of rheumatic diseases," Biodrugs, vol. 18, pp. 95-102, (2004).
Daoussis, D., et al., "Targeting CD40L: a promising therapeutic approach," Clinical and Diagnostic Laboratory Immunology, pp. 635-641, (Jul. 2004).
Molano, R.D., et al., "Prolonged islet graft survival in NOD mice by blockade of the CD40-CD154 pathway of t-cell costimulation," Diabetes, vol. 50, pp. 270-276, (Feb. 2001).
Quezada, S.A., et al., "Mechanisms of donor-specific transfusion tolerance: preemptive induction of colonal T-cell exhaustion via indirect presentation," Blood, vol. 102, No. 5, pp. 1920-1926, (Sep. 2003).

(Continued)

*Primary Examiner* — Cecilia J Tsang
*Assistant Examiner* — Ronald Niebauer
(74) *Attorney, Agent, or Firm* — Jacobson Holman PLLC

(57) ABSTRACT

The invention refers to a synthetic peptide comprising an amino acid sequence of seven residues in length, preferably flanked by 2 cysteine residues at both ends, which is capable of specifically recognizing human CD154 and blocking CD40:CD154 interaction, thereby inhibiting the biological effects depending on such interaction. The peptide of the invention, which is preferably in a cyclic form, is suitable for use for diagnostic and therapeutic applications, especially for the diagnosis and therapy of tumor, inflammatory diseases and transplant rejection.

20 Claims, 10 Drawing Sheets

(56) References Cited

OTHER PUBLICATIONS

Figure 1:
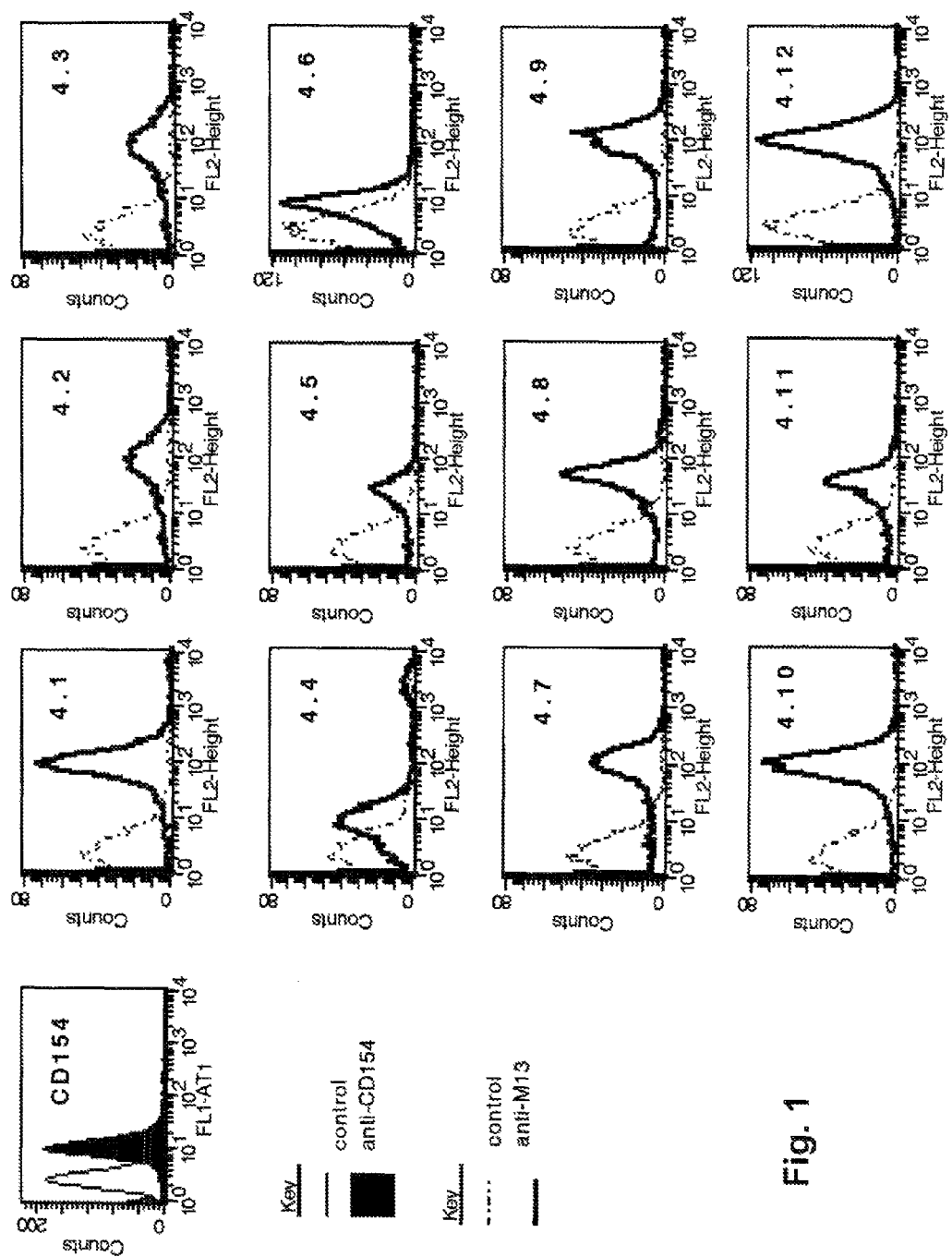

Elster, E.A., et al., "The road to tolerance: renal transplant tolerance induction in nonhuman primate studies and clinical trials," Transplant Immunology, vol. 13, pp. 87-99, (2004).

Xu, H., et al., Platelet-derived or soluble CD154 induces vascularized allograft rejection independent of cell-bound CD154, The Journal of Clinical Investigation, vol. 116, pp. 1-6, (2006).

Snanoudj, R., et al., "Costimulation blockade and its possible future use in clinical transplantation," Transplant International, vol. 19, pp. 693-704, (2006).

Nanji, S.A., et al., "Costimulation blockade of both inducible costimulator and CD40 ligand induces dominant tolerance to islet allografts and prevents spontaneous autoimmune diabetes in the NOD mouse," Diabetes, vol. 55, pp. 27-33, (Jan. 2006).

Allen, S.D., et al., "Therapeutic peptidomimetic strategies for autoimmune diseases: costimulation blockade," J. Peptide Res., vol. 65, pp. 591-604, (2005).

Ladner, R.C., et al., "Phage display-derived peptides as therapeutic alternatives to antibodies," Therapeutic Focus, DDT, vol. 9, No. 12, pp. 525-529, (Jun. 2004).

Hetian, L., et al., "A novel peptide isolated from a phage display library inhibits tumor growth and metastasis by blocking the binding vascular endothelial growth factor to its kinase domain receptor," The Journal of Biological Chemistry, vol. 277, No. 45, pp. 43137-43142, (2002).

Kelsoe, G., "Therapeutic CD154 antibody for lupus promise for the future?" Journal of Clinical Investigation, vol. 112, No. 10, pp. 1480-1482, (Nov. 2003).

Langer, F., et al., "The role of CD40 in CD40L- and antibody-mediated platelet activation," Thromb Haemost, vol. 93, pp. 11-37-46, (2005).

* cited by examiner

HUMAN CD154-BINDING SYNTHETIC PEPTIDE AND USES THEREOF

This is a national stage of PCT/EP08/066,349 filed Nov. 27, 2008 and published in English, which has a priority of European no. 07122164.2 filed Dec. 3, 2007, hereby incorporated by reference.

The present invention relates to a synthetic peptide which is capable of binding to human CD40 ligand (CD40L or CD154). In particular, the present invention relates to a synthetic peptide having an amino acid sequence which is capable of specifically binding to the active site of CD154, thereby inhibiting the interaction between CD154 and its natural ligand CD40 as well as the biological effects depending on such an interaction. The invention also relates to the uses of the peptide in the diagnosis and therapy of diseases having an inflammatory, immune or hematological origin.

CD40 is a molecule constitutively expressed on the surface of B cells, where it plays a crucial role during the maturation process. CD40 is also expressed on the surface of a number of further cell types, including monocytes, fibroblasts, dendritic cells, endothelial cells, smooth muscle cells and epithelial cells (van Kooten et al, J. Leukoc. Biol. 2000). Its ligand, CD154 (also designated as CD40L), is transiently expressed upon activation on the surface of T cells, macrophages, platelets, monocytes, NK cells and endothelial cells. In particular, the interaction between CD40 expressed on the surface of B cells and CD154 expressed on the surface of activated T cells, leads to clonal expansion and isotype switching of B cells, resulting in their transformation into plasmacytes.

The importance of the CD40:CD154 interaction in the development of an effective immune response is shown by the fact that a mutation in the CD154 coding gene is responsible for a severe human form of immunodeficiency, the hyper IgM syndrome (HIM), characterized by overproduction of IgM but the absence of IgG, IgA and IgE, and accompanied by severe recurrent infections (Aruffo A. et al, Cell 1993).

In the last years, many studies have demonstrated the involvement of the CD40:CD154 interaction in many processes with an inflammatory etiogenesis, such as atherosclerosis, autoimmune diseases, post-transplant rejection, graft-versus host disease, etc. (Schonbeck U. et al, Circ. Res. 2001; Henn V. et al, Nature 1998; Biancone L. et al, Int. J. Mol. Med. 1999; Buchner K. et al, J. Pathol. 2003). The expression of CD40 or its ligand CD154 or the co-expression of both molecules, has also been demonstrated in many tumors, suggesting the involvement of this signaling pathway in tumor development (Bussolati B. et al, Int. J. Cancer 2002; Biancone L. et al, J. Immunol. 1999; Cantaluppi V. et al, Int. J. Immunopathol. Pharmacol. 2006; Hill S. C. et al, J. Immunol. 2005; Melichar B. et al, Gynecol. Oncol. 2007; Eliopoulos A. G. et al, Curr. Opin. Pharmacol. 2004). In particular, the CD40:CD154 signaling pathway is deemed to be involved in the progression of Chronic Lymphocytic Leukemia (CLL), in that it has been shown to promote both tumor cell survival and the pro-angiogenic properties of endothelial cells (Dicker F. et al, Blood 2006).

A number of approaches aimed at inhibiting the CD40:CD154 interaction were developed in order to provide novel therapeutic opportunities. In particular, promising results were obtained in different experimental models of autoimmune diseases, atherosclerosis and transplant rejection. The inhibition of the CD40:CD154 interaction through an anti-CD154 monoclonal antibody-based approach provided clinical improvements in many models of autoimmune diseases, such as systemic lupus erythematosus (SLE), reumathoid arthritis (RA), psoriasis and Crohn's disease (Boumpas D. T. et al, Arthritis Rheum. 2003; Liossis S, N. et al, Bio Drugs 2004; Daoussis D. et al, Clin. Diagn. Lab. Immun. 2004). Anti-CD154 antibodies are also disclosed in the patent literature. WO 2005/003175 discloses aglycosyl anti-CD154 antibodies; WO 2006/033702 discloses anti-CD154 antibodies and peptides, particularly light chain and heavy chain variable regions of antibodies. Furthermore, a number of papers demonstrated that the use of monoclonal antibodies in mice following islet, skin, bone marrow, heart and kidney transplantation leads to prolonged survival of the transplanted organs (Molano R. D. et al, Diabetes 2001; Quezada S. A. et al, Blood 2003; Elster E. A. et al, Transpl. Immunol. 2004; Xu H. et al, J. Clin. Investig. 2006; Snanoudj R. et al, Transpl. Int. 2006; Nanji S. A. et al, Diabetes 2006). Costimulation blockade may be achieved with monoclonal antibodies, Fab fragments or fusion proteins directed against the costimulatory molecules. However, the results of these approaches are often compromised by the risk of immunogenic effects and pro-thrombotic side effects, which are due to the recognition of the Fc fraction (Henn V. et al, Nature 1998), and by poor tissue penetration and immunosuppression. To lower inherent immunogenicity, humanized and mini-antibodies were developed, but unfortunately at the cost of affinity.

One object of the present invention is to provide a reagent which is capable of inhibiting the CD40:CD154 interaction and blocking the biological effects depending on such an interaction, and which overcomes the limitations and drawbacks of the prior art, in particular those related to the use of monoclonal anti-CD154 antibodies.

This object is achieved by a synthetic peptide, which is preferably in a cyclic form, which is capable of specifically binding to the active site of human CD154 (also designated as human CD40L).

The peptide of the invention comprises the hepta-amino acid CD154-binding sequence designated as SEQ ID NO: 13 in the sequence listing.

According to a preferred embodiment, the peptide of the invention is from 7 to 30 amino acids in length.

According to an even more preferred embodiment, the peptide of the invention consists of the nona-amino acid sequence designated as SEQ ID NO:6 in the sequence listing, resulting from the addition of flanking cysteine residues at both ends of the hepta-amino acid CD154-binding sequence designated as SEQ ID NO:13. This embodiment is particularly advantageous in that SEQ ID NO:6 is capable of undergoing cyclization by formation of a disulfide bond between the two terminal cysteines.

The peptide according to the invention has the advantage that it is not capable of inducing unwanted immune responses in the patient to which it is administered.

According to a further embodiment, the peptide of the invention is provided in the form of a multimeric peptide structure comprising a plurality of copies of the peptide, each of the said peptide copies being either in a linear or in a cyclic form. The multimeric peptide structure is preferably a tetrameric structure. The multimeric peptide structure preferably consists of a plurality of copies of the peptide, wherein each copy is bound to at least one other copy by at least one amino acid spacer, which is preferably a G (Gly) residue, and in which each of the peptide copies is directly or indirectly bound to an amino acid core, which preferably consists of three K (Lys) residues.

A particularly preferred multimeric peptide structure according to the invention is represented below:

```
          G-LPTRHMA
       K
      /   G-LPTRHMA
    K
      \   G-LPTRHMA
       K
          G-LPTRHMA
``` wherein L is Leu, P is Pro, T is Thr, R is Arg, H is His, M is Met, A is Ala, G is Gly and K is Lys.

The above-illustrated multimeric structure was shown to exert, at a 60 µM concentration, the same inhibitory activity on CD40 stimulation by recombinant soluble CD154 as peptide 4.10, even though it contains the CD154-binding sequences SEQ ID NO:13 in a linear form. Moreover, the tetrameric structure, like peptide 4.10, resulted inactive in activating human platelet aggregation with thrombin at a subliminal dose (0.3 U/ml). These results indicate that the CD154-binding sequence (SEQ ID NO:13) is capable of binding to CD154 and of exerting its biological function either when it is in a cyclic form and when it is in a linear form. While the cyclic peptide has the advantage of protecting the amino acid sequence from proteolysis (e.g. in plasma), the possibility of designing multimeric forms of the peptides allows to modulate the molecular size, the rate of clearance and consequently the half-life.

As mentioned hereinbefore, the scope of the invention also includes the use of a peptide or a multimeric structure according to the invention, in diagnostic and therapeutic applications.

The scope of the invention further includes conjugates wherein the peptide or multimeric peptide structure of the invention is linked to a diagnostic agent (e.g., a detectable molecule for in vivo or in vitro assay) or a therapeutic agent (e.g., an anti-inflammatory drug, an anti-tumor drug, or a cytotoxic agent capable of exerting a cytotoxic effect on activated endothelial cells, tumor cells or any other cell which is capable of expressing CD154 at the cell surface upon activation) to enable in vivo or in vitro detection and for the preparation of a medicament for the treatment of a number of diseases or disorders related to CD40:CD154 interaction. Examples of such diseases or conditions are inflammatory disease (such as e.g. atherosclerosis, autoimmune diseases, transplant rejection, inflammations associated with arthritis, contact dermatitis, hyper-IgE syndrome, inflammatory bowel disease, allergies, including allergic asthma, idiopathic inflammatory disease), tumor diseases (e.g. Chronic Lymphocytic Leukemia), graft-versus-host disease. Examples of autoimmune diseases are systemic lupus erythematosus (SLE), rheumatoid arthritis (RA), Crohn's disease, psoriasis. The peptide or multimeric structure or conjugate of the invention is also suitable for use for the induction of immunotolerance.

Synthetic peptides represent an alternative approach to mAbs in order to inhibit the interaction between molecules. The theory behind the use of synthetic peptides is that proteins only exert their biological effects via small external regions, only a few amino acids of which are essential to proper receptor functioning. Thus, the sequences corresponding to these regions can be synthesized in a shorter, conformationally correct version retaining the essential amino acid residues. In this manner, it is possible to obtain a short peptide which specifically recognizes the active site of the target receptor, but which is biologically inactive and which provides steric hindrance, thereby preventing the interaction between the receptor and the native protein. The major theoretical advantage of such peptides, which are capable of mimicking the interaction between the agonist and the receptor, is their limited size which makes them readily soluble in water and non-immunogenic, allowing them to be administered for longer periods of time (Allen S. D. et al, J. Peptide Res. 2005; Ladner R. C. et al, DDT 2004).

However, the identification of an amino acid sequence capable of effectively inhibiting the CD40:CD154 interaction is not an obvious result. As it will be illustrated in greater detail below, even the modification of a single amino acid residue of the peptide sequence of the invention (SEQ ID NO:13 or SEQ ID NO:6) actually results in the loss of the ability to bind to the active site of human CD154 and, consequently, to the loss of the inhibiting ability of the peptide.

As mentioned before, the peptide according to the invention comprises the amino acid sequence designated as SEQ ID NO: 13 or the peptide sequence designated as SEQ ID NO:6 in the sequence listing. Such a peptide shows a very high binding specificity to the active site of human CD154. It is capable of recognizing and binding the active site of CD154 and, as a consequence, of effectively blocking the receptor both in vivo and in vitro, so as to inhibit the biological effects resulting from such an interaction. In the following description, the peptide according to the invention consisting of SEQ ID NO:6 shall be designated as "peptide 4.10".

The results illustrated in the following experimental section show that peptide 4.10 of the invention is capable of preventing the activation of CD40 on B cells induced by stimulation with a recombinant soluble form of human CD154 (recombinant human soluble CD154, or rhsCD154). The interference exerted on the CD40:CD154 interaction prevents both B cells activation and the resulting immune response. The inventors have demonstrated that peptide 4.10 is capable of inhibiting the induction of other co-stimulatory molecules, such as CD80 and CD86, on B cells, as well as the isotype switching of immunoglobulins. Furthermore, peptide 4.10 is capable of blocking the rhsCD154-induced activation of endothelial cells in vitro, evaluated as the ability of the cells of migrating and forming vascular-like structures. Such an anti-angiogenic activity of peptide 4.10 is still more evident in vivo in a murine angiogenesis Matrigel model in SCID mice, which is described in greater detail below. Finally, preliminary data obtained by the inventors show that peptide 4.10 is capable of inducing drastic apoptosis in B cells from CLL patients.

Further details on the preparation and administration techniques of conjugates and pharmaceutical compositions comprising short peptides are known in the prior art; a detailed description thereof is not necessary herein, since it would not be essential to the comprehension of the invention.

As it will be illustrated in the following experimental section, the present description illustrates the identification of 7 amino acid sequences which are specifically directed against human CD154. In particular, seven cyclic hepta-peptides capable of binding human CD154 were selected and characterized. A fusion protein comprising the N-terminal domain of human CD154 was employed to select the peptides. Among the seven selected and characterized hepta-peptides, the only one which actually proved to be capable of inhibiting the CD40:CD154 interaction is peptide 4.10 of the invention. Furthermore, the amino acid sequence of peptide 4.10 was modified by mutation of 1 or 2 amino acid residues in an attempt to select useful alternative forms to peptide 4.10. However, none of the alternative forms retained the ability to inhibit the CD40:CD154 interaction, nor the biological effects related to such an interaction.

The following detailed description is provided by way of illustration only, with reference to the annexed drawings and the tables provided below, wherein:

The histograms of FIG. 1 show the binding of the selected phage clones to the J558L cells, that is a murine myeloma cell line transfected for the expression of human CD154 on the cell surface. Binding of the selected phages to the cells was demonstrated by flow cytometry, by incubation of the J558L cells with the phages and then with an anti-M13 monoclonal antibody. For each experimental condition, 10,000 events were analyzed and the values are the mean and standard deviation of 3 different experiments. All of the 12 selected clones bind to the J558L cells.

Table I shows the 7 amino acid sequences of the peptide inserts obtained from the human CD154-binding clones. The inserts of the clones designated as 4.1, 4.5 and 4.9 were lost due to recombination, whilst the inserts of the clones designated as 4.2 and 4.3 and those of the clones designated as 4.7 and 4.12 proved to be identical.

Figure 2:
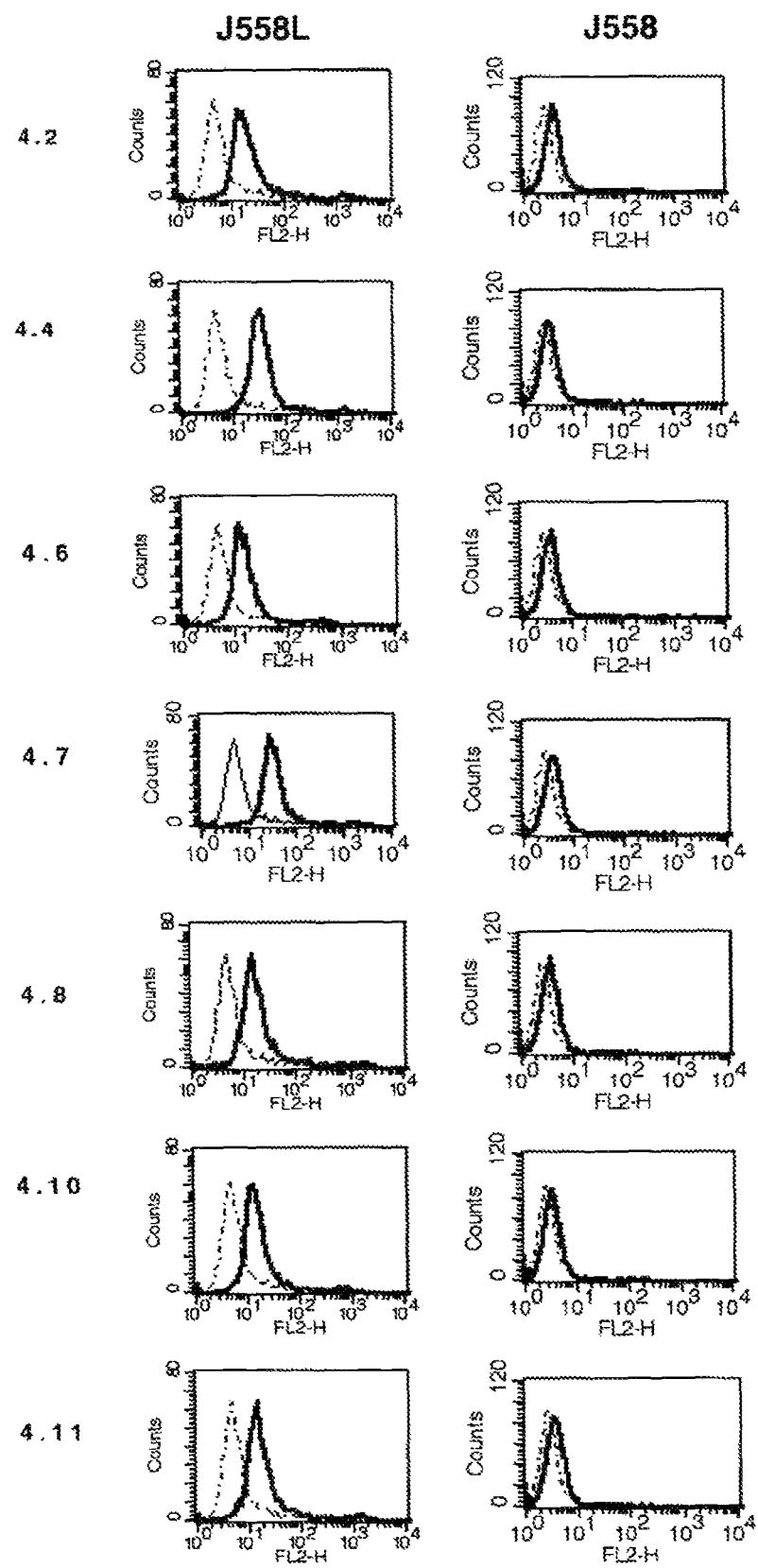

FIG. 2 represents the binding of the seven peptides obtained from the human CD154-binding clones and tagged with a 6 histidines tail (-$His_6$) to the J558L $CD154^+$ cells. Binding of the peptides to the cells was demonstrated by flow cytometry. The cells were incubated with each of the -$His_6$-tagged peptides and then with a phycoerythrin-conjugated secondary antibody specific for the -$His_6$ tail. The dotted histogram is the isotopic control, whilst the black line is the binding intensity of the CD154-specific peptides [4.2=4.3=CPSGHTKAC (SEQ ID NO: 1), 4.4=CGTHSSRIC (SEQ ID NO: 2), 4.6=CLGTQNKEC (SEQ ID NO: 3), 4.7=4.12=CTPGKPHSC (SEQ ID NO: 4), 4.8=CKAASANIC (SEQ ID NO: 5), 4.10=CLPTRHMAC (SEQ ID NO: 6) and 4.11=CLSAVHNMC (SEQ ID NO: 7)]. For each experimental condition, 10,000 events were analyzed and the values are the mean and standard deviation of 3 different experiments. All of the peptides are capable of specifically binding to the CD154 on the J558L $CD154^+$ cells and are not capable of binding to the control J558 cells.

Figure 3:
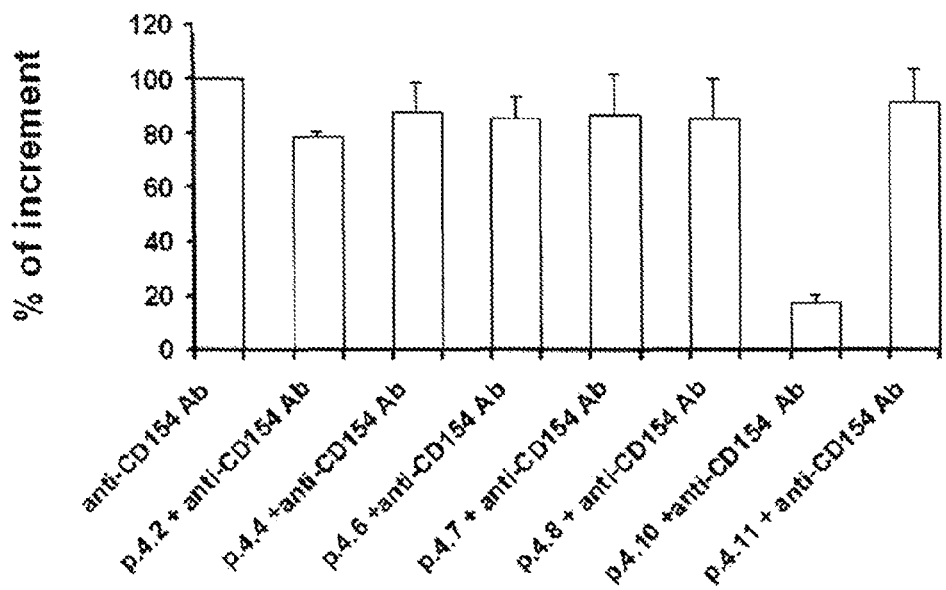
Figure 3:
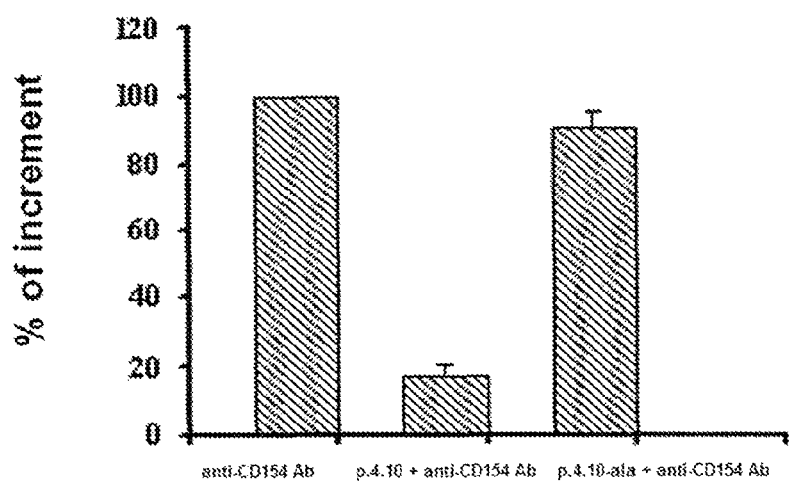

FIG. 3A shows the competition between the anti-CD154 peptides and an anti-human CD154 fluorescein-conjugated antibody specific for the active site of CD154. The murine myeloma cells transfected with human CD154, J558L, were incubated with each of the seven anti-CD154 peptides tagged with a 6 histidines tail (-$His_6$), and then with the anti-CD154 fluorescein-conjugated antibody. The ability of the peptides to compete with the anti-CD154 antibody for the binding to the CD154 molecule expressed on the surface of the J558L cells was evaluated by flow cytometry, as the reduction in the fluorescence intensity compared to the positive control represented by cells incubated with the anti-human CD154 fluorescein-conjugated antibody alone. It is clear from the figure that peptide 4.10 (SEQ ID NO: 6) is the only one which is capable of competing with the anti-human CD154 antibody and significantly displacing its binding. FIG. 3B shows the comparison between peptide 4.10 (SEQ ID NO: 6) and peptide 4.10-ala (SEQ ID NO: 8), which is used as a control. The amino acid sequence of the control peptide differs from that of peptide 4.10 in that an arginine residue is replaced with an alanine residue at amino acid position 5. The arginine residue is clearly essential, since its absence results in the complete inactivation of the peptide's ability to compete with the anti-CD154 fluorescein-conjugated antibody for human CD154, as FIG. 3B clearly shows.

Figure 4:
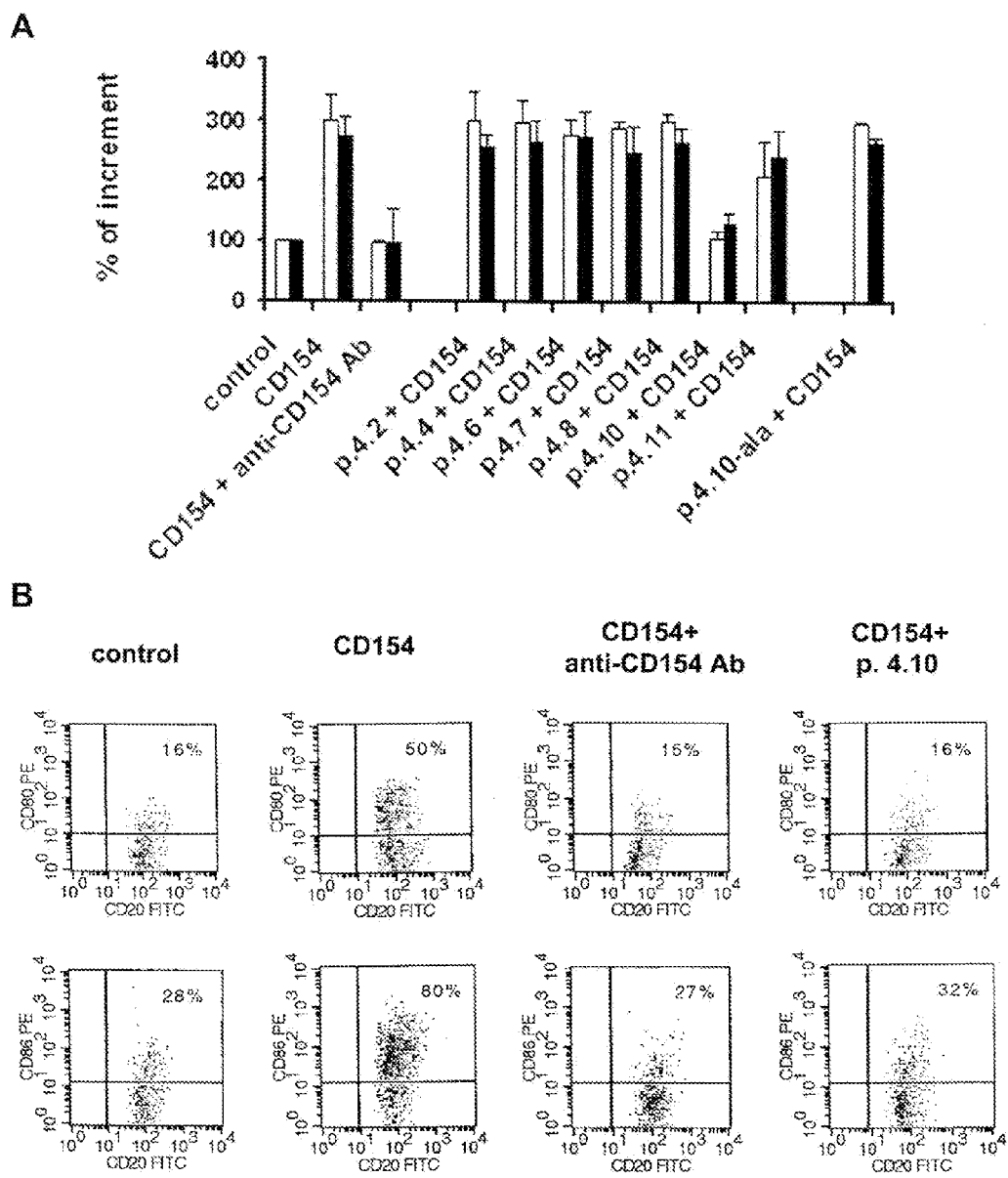

The histograms of 4A show the effect of the anti-CD154 peptides and the control peptide 4.10-ala, on the activation B cells induced by stimulation with a soluble recombinant human CD154 molecule (rhsCD154). B cells were stimulated for 48 hours with rhsCD154 in the absence and in the presence of a blocking anti-human CD154 antibody or one of the seven selected peptides. Peripheral B cell activation was evaluated by flow cytometry, as the membrane expression of the co-stimulatory molecules CD80 and CD86. As FIG. 4A clearly shows, stimulation of B cells for 48 hours with human soluble CD154 (rhsCD154) induces strong expression of CD80 and CD86 on the cell surface. On the contrary, the activation is prevented when rhsCD154 is used in combination with a blocking anti-human CD154 antibody or with peptide 4.10 (SEQ ID NO: 6). None of the remaining peptides is capable of significantly inhibiting the rhsCD154-induced activation of B cells. FIG. 4B shows the details of the cytometric analysis.

Figure 5:
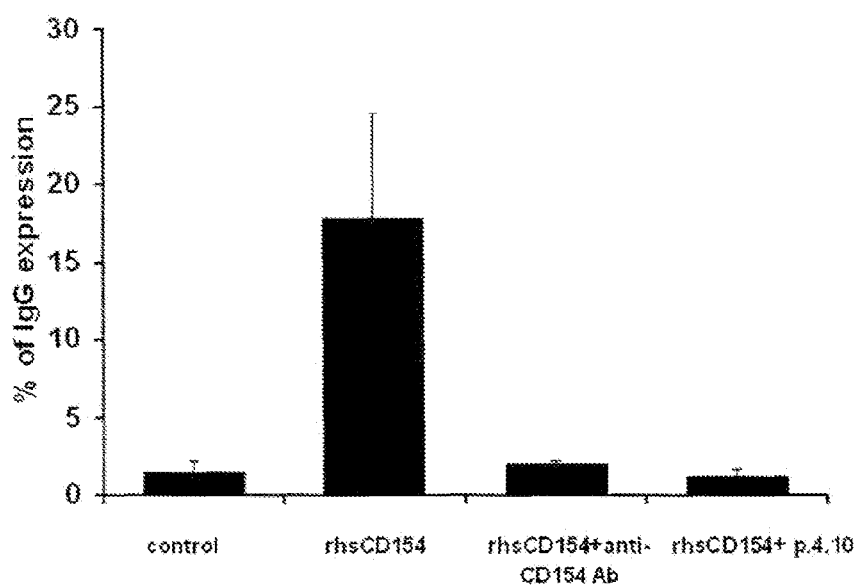
Figure 5:
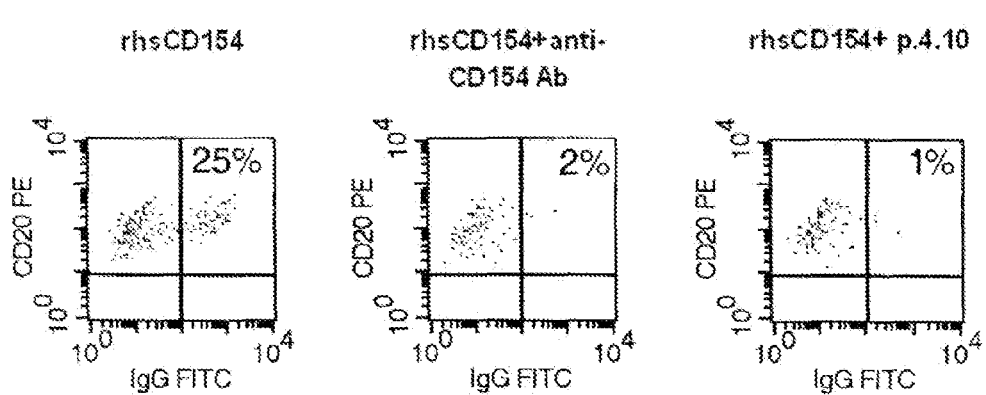

The graphics of FIG. 5A show the percentage of naive B cells undergoing isotype switching and expressing IgG, under basal condition with no stimulation, after stimulation for 72 hours with IL4 and CD154, after stimulation for 72 hours with IL4 and CD154 in combination with a blocking anti-human CD154 antibody, or after stimulation for 72 hours with IL4 and CD154 in combination with peptide 4.10 (SEQ ID NO: 6), respectively. Peptide 4.10 (SEQ ID NO: 6), just as the anti-CD154 antibody, is capable of strongly inhibiting the isotype switching of immunoglobulins induced by stimulation with rhsCD154 and IL4. FIG. 5B shows the details of the cytometric analysis.

Figure 6:
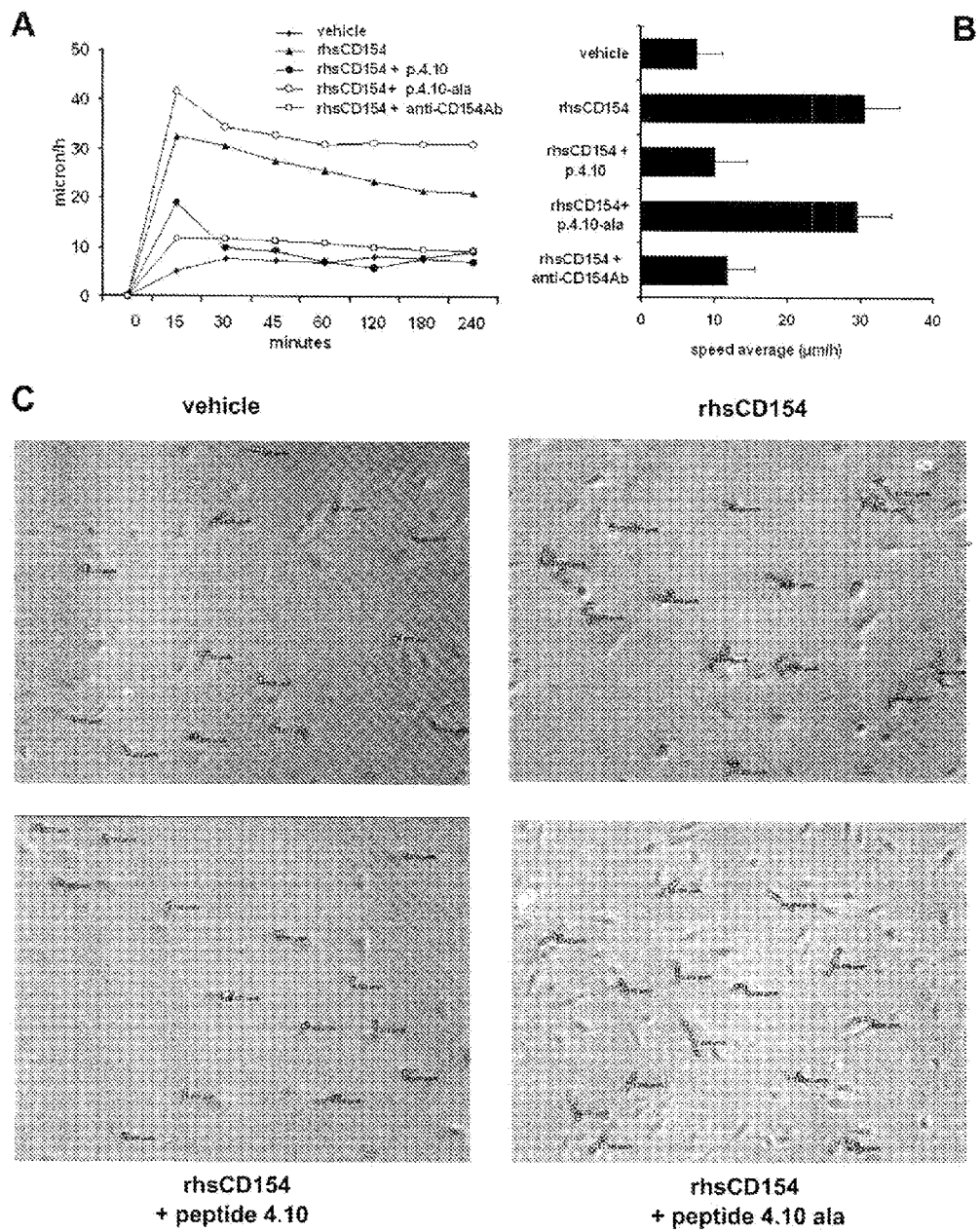

FIG. 6 shows the effects of the CD154-induced stimulation on the motility of HUVECS (HUVECs=human umbilical vein endothelial cells) in the absence or presence of peptide 4.10 (SEQ ID NO: 6), or of the control peptide 4.10-ala (SEQ ID NO: 8), or of a blocking anti-human CD154 antibody. In particular, FIG. 6A shows the time-lapse kinetics of cell migration under various experimental conditions over a period of 4 hours; FIG. 6B shows the differences observed in cell migratory speed after stimulation for 30 minutes under the above-mentioned experimental conditions; FIG. 6C shows representative images of the time-lapse analysis. Peptide 4.10 (SEQ ID NO: 6), contrary to control peptide 4.10-ala (SEQ ID NO: 8), inhibits the rhsCD154-induced motility of endothelial cells.

Figure 7:
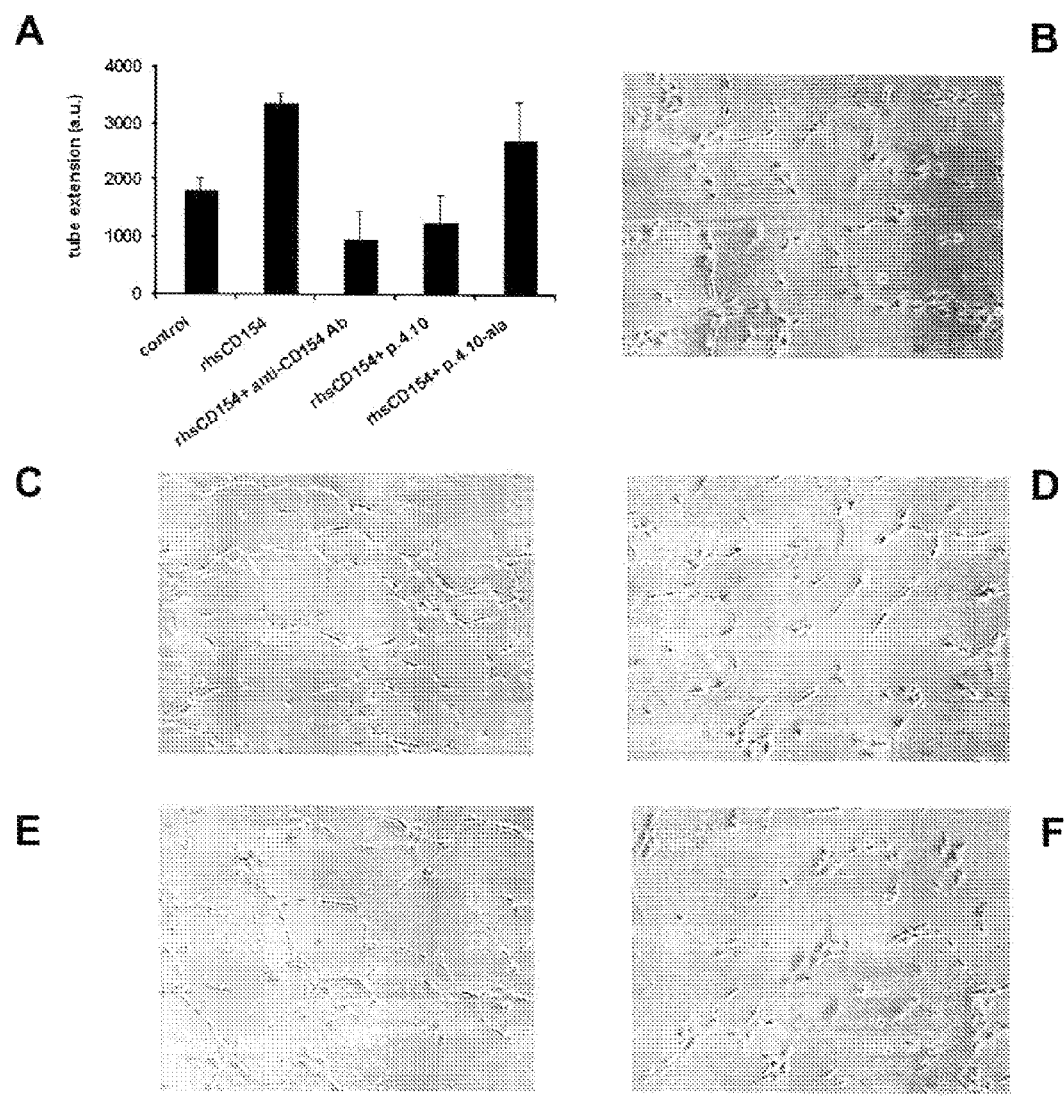

FIG. 7A shows the ability of Matrigel-plated HUVECs to form vessel-like cell cords under basal conditions with no stimulation or after stimulation with rhsCD154 in the presence/absence of either a blocking anti-human CD154 antibody, or peptide 4.10 (SEQ ID NO: 6), or the control peptide 4.10-ala (SEQ ID NO 8). FIGS. 7B-F show representative images of cell cord formation ability on Matrigel under the various experimental conditions mentioned above (B=unstimulated control; C=rhsCD154; D=rhsCD154+ 4.10 peptide; E=rhsCD154+ 4.10-ala peptide; F=rhsCD154+ blocking anti-CD154 antibody). Peptide 4.10 of the invention (SEQ ID NO: 6), contrary to control peptide 4.10-ala (SEQ ID NO: 8), inhibits the rhsCD154-induced ability of the endothelial cells of forming cell cords.

Figure 8:
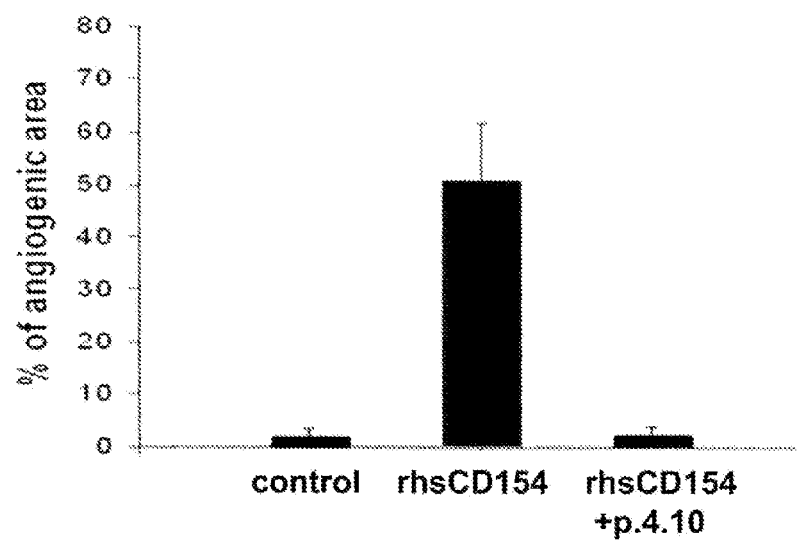
Figure 8:
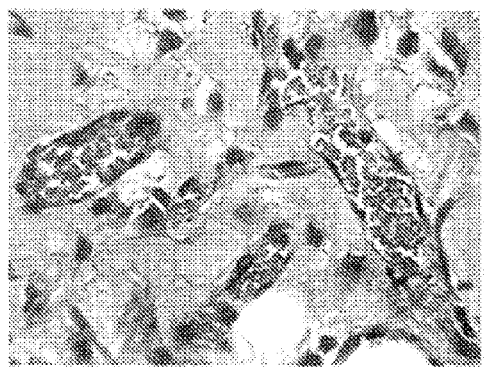
Figure 8:
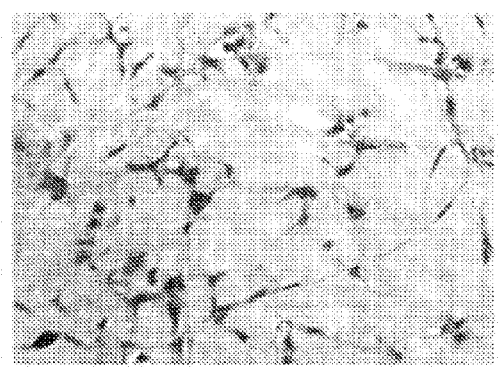

FIG. 8 shows the in vivo effect of rhsCD154-induced stimulation in the presence/absence of peptide 4.10 (SEQ ID NO: 6), on endothelial HUVEC cells subcutaneously inoculated into the hip of SCID mice in combination with 250 µl of Matrigel. 7 days after inoculation, the mice were killed and the grafts were taken, fixed in 10% formalin solution, embedded in paraffin and prepared for histological analysis. FIG. 8A shows the quantization, on hematoxylin-eosin stained histological sections, of the vascularized region under basal conditions and under the other experimental conditions mentioned above. FIGS. 8B and 8C are two representative images of the angiogenesis obtained upon stimulation of endothelial cells with rhsCD154 alone or with rhsCD154 in combination with peptide 4.10 (SEQ ID NO: 6), respectively. Six SCID mice were used for each experimental condition. Peptide 4.10 completely inhibits rhsCDl54-induced angiogenesis in vivo.

Figure 9:
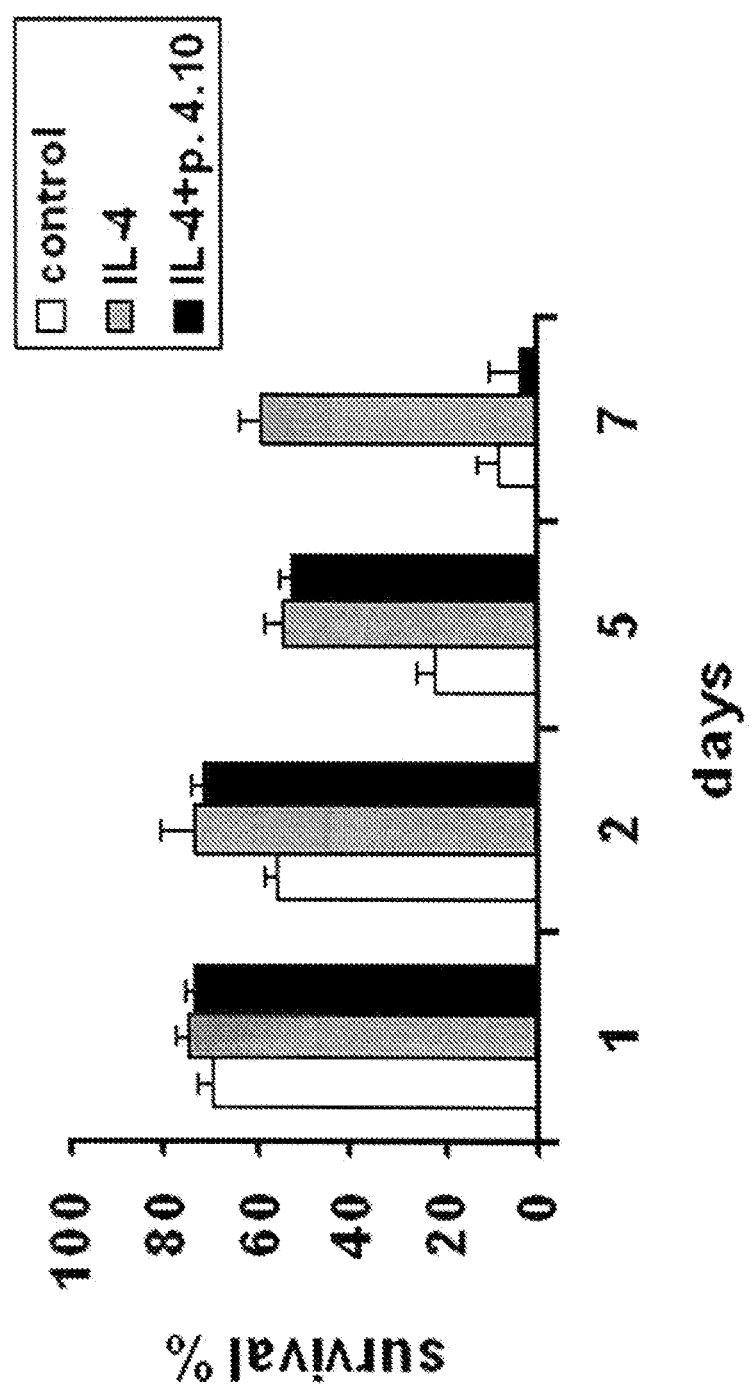

FIG. 9 shows the ability of peptide 4.10 of the invention (SEQ ID NO: 6) of inhibiting the survival of CLL cells induced by IL-4 stimulation.

Figure 10:
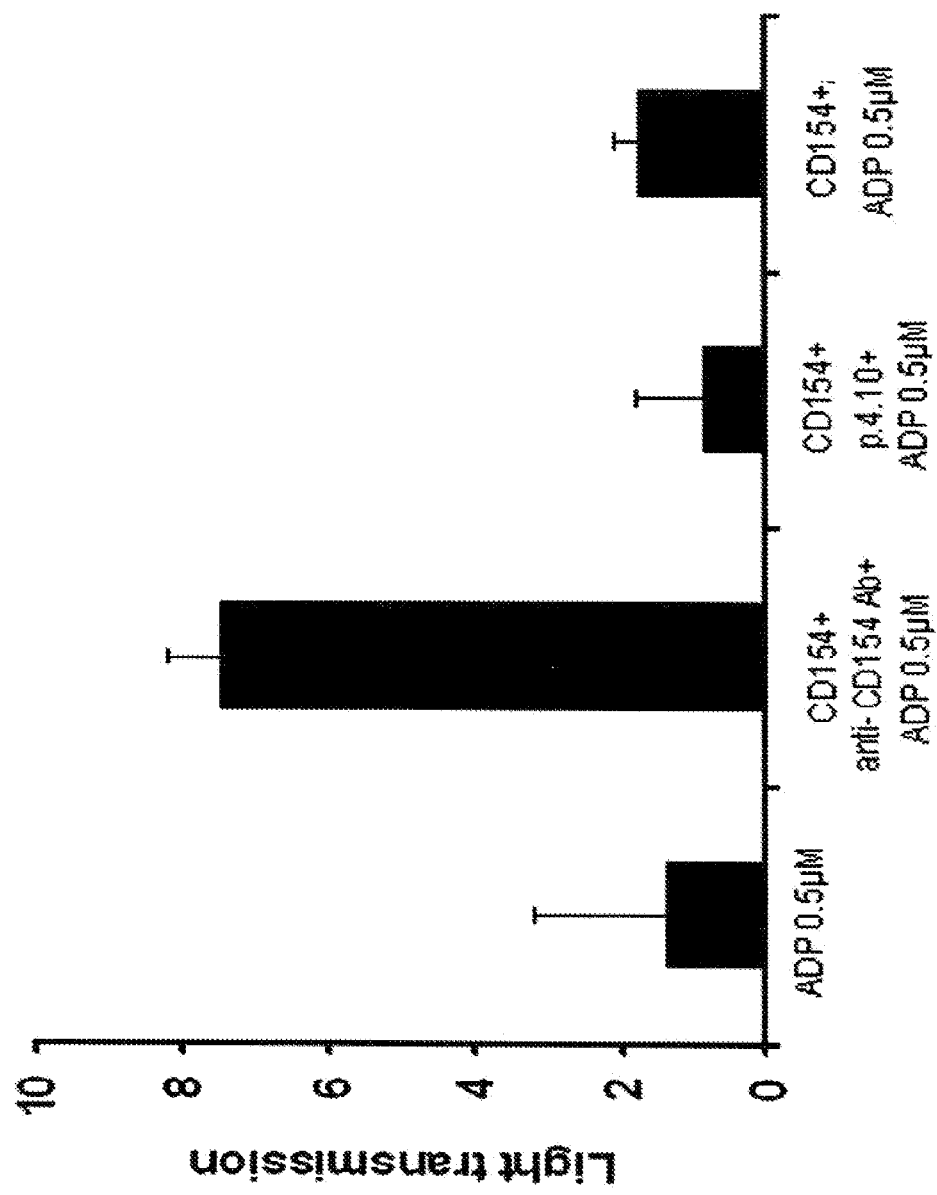

FIG. 10 shows human platelet aggregation upon stimulation with ADP 0.5 µM alone or stimulation with ADP 0.5 µM preceded by stimulation for 10 minutes at 37° C. with rhsCD154, or rhsCD154 in combination with peptide 4.10 (SEQ ID NO: 6), or rhsCD154 in combination with an immunocomplex consisting of rhsCD154 and an anti-human CD154 antibody. Platelet aggregation was measured with an aggregometer, as the increase in light transmission compared to the control. Priming of human platelets with the anti-human CD154 antibody in combination with rhsCD154 increases platelet aggregation upon stimulation with ADP 0.5 µM. In contrast, rhsCD154 alone or in combination with peptide 4.10, does not affect the platelet aggregation levels induced upon stimulation with ADP 0.5 µM. These results show that the interaction between peptide 4.10 of the invention (SEQ ID NO: 6) and the CD154 molecule does not induce platelet aggregation, which on the contrary, is induced by the interaction with the anti-CD154 antibody.

The following experimental section is provided by way of illustration only and it is not intended to limit the scope of the invention as defined by the appended claims.

Experimental Section

Throughout this study, a peptide library expressed in M13 phages consisting of a panel of peptide sequences (peptide variability <$10^9$) of 7 amino acid residues with 2 flanking cysteines at both ends enabling cyclization by disulfide bonds, genetically fused to the capside pIII phage protein and randomly expressed on the phage surface, was used. The phage library was screened by the biopanning in vitro model developed by the present inventors from a previously known model (Hetian L. et al, J. Biol. Chem. 2002). The phages ($1\times10^{11}$ CFU in 200 µl of TBS) were incubated for 1 hour at room temperature with human recombinant CD154, previously adhered to a plate. The phages were washed several times with TBS-T to remove CD154-unbound unspecific phages, the phages bound to CD154 were collected by elution with 100 µl of 0.2 M glycine, pH 2.2, neutralized after 10 minutes with 15 µl of 1 M Tris-HCl, pH 9.1. The phage number was evaluated by titration, adding serial dilutions of the eluate to host tetracycline-resistant *Escherichia coli* ER2738 cells (New England Biolabs, Hitchin, U.K.) on LB agar (agarose 7 g/liter, $MgCl_2.6H_2O$ 1 g; Sigma), and plating on IPTG/X-Gal LB agar in the presence of tetracycline (Kramel Biotech, Cramlington, U.K.). After incubation for 12 hours at 37° C., the number of phage colonies, visible on the plate as blue plaques, was counted. The eluated phages was amplified by culturing the phages on IPTG/X-Gal LB agar plates in the presence of tetracycline and picked up and precipitated by centrifugation in 3.3% polietilen glycol 8,000/0.4 M NaCl (Sigma). The phages were then titrated, as described above, and re-incubated on a novel plate coated with human recombinant CD154. The screening and amplification process was repeated four times to enrich the library of human CD154-specific phage clones. After the fourth amplification round, 12 phage clones were randomly selected, individually expanded and tested for their ability to recognize CD154 expresses on the cell surface. Specific binding of the individual selected clones was demonstrated in vitro by flow cytometry, using a murine myeloma cell line transfected for the expression of human CD154, designated as J558L, as the reference cell line. Binding of the phages ($10^{11}$ cfu) to J558L cells, following incubation for 30 minutes to room temperature, was detected by flow cytometry, by indirect immunofluorescence incubating the cells with a monoclonal antibody against the phage protein M13 (Pharmacia, Uppsala, Sweden) and subsequently with an anti-mouse phycoerythrin-conjugated antibody (Sigma). As shown in FIG. 1, all of the 12 phage clones were capable of specifically binding human CD154-expressing cells (J558L), but they did not bind to the control CD154-negative (J558) cells.

Sequencing of the peptide insert of the 12 phage clones the 7 different sequences listed in table I were obtained. The peptides were synthesized and conjugated with biotin (-bio) or with a 6-histidine tail (-$his_6$) so as to enable in vitro and in vivo localization. Likewise, binding of the peptides to the J558L cells was demonstrated by flow cytometry incubating the cells for 30 minutes at room temperature with the -$his_6$-tagged peptides (-$his_6$ peptides-60 µM) and subsequently for 30 minutes at 4° C. with an anti-poly hystidine-phycoerythrin-conjugated antibody (Sigma). All of the seven selected peptides showed good affinity towards the J558L CD154$^+$ cells, whilst they did not bind to the control cells J558 (FIG. 2). Furthermore, a competition assay between the peptides and an anti-human CD154 fluorescein-conjugated antibody (Serotec) specifically recognizing the active site of CD154 was carried out. The J558L cells were incubated with the $his_6$-peptides for 30 minutes at room temperature and then with anti-human CD154 fluorescein-conjugated antibody for another 30 minutes at room temperature. FIG. 3A shows that peptide 4.10 is the only one which is capable of significantly inhibiting the interaction between the anti-human CD154-fluorescein-conjugated antibody and the J558L cells. In order to identify the amino acid residues of the amino acid sequence of peptide 4.10 which are essential to the binding to CD154, three different peptides were synthesized, each one carrying a point mutation, which amino acid sequences differ from that of peptide 4.10 by replacement of the amino acid residues at positions 4, 5, 6, respectively, with one alanine residue.

The mutated peptides were not capable of recognizing human CD154 expressed at the surface of J558L cells (data not shown). The least reactive peptide, having the amino acid sequence CLPTAHMAC (SEQ ID NO: 8), designated as 4.10-ala, was selected as the control peptide (FIG. 3B).

Similar results were obtained with the four modified peptides 4.101, 4.102, 4.103 e 4.104 having the amino acid sequences illustrated in table II. None of these peptides proved to be capable of binding to human CD154 expressed on the surface of CD154$^+$ J558L cells (data not shown).

B cells are known to constitutively express the CD40 molecule on the cells membrane (van Kooten C. et al, J. Leukoc. Biol. 2000). Stimulation of CD40 by CD154-expressing activated T cells, results in B cells activation, proliferation and isotype switching. The inventors employed B cells isolated from whole peripheral blood of healthy donors by gradient-Ficoll centrifugation and immunomagnetical separation (MACS systems—Milteniy). The quiescent B cells thereby obtained, were then stimulated with a soluble form of human recombinant CD154 (rhsCD154) to induce activation and expression of the co-stimulatory molecules CD80 (B7-1) and CD86 (B7-2) on the cell membrane. A drastic increase in membrane expression of CD80 and CD86 on the cell surface of peripheral B cells, after stimulation for 48 hours with rhsCD154 (100 ng/ml) was observed. The expression was increased by 300% and 274%, respectively, compared to basal levels. In contrast, pre-incubation for 15 minutes at 37° C. of rhsCD154 (100 ng/ml) with peptide 4.10 (SEQ. ID NO: 6), prior to lymphocyte stimulation, blocked B cells stimulation and the related expression of CD80 and CD86. The inhibitory effect of peptide 4.10 (SEQ. ID NO: 6) peaked at the concentration of 60 μM, with a reduction in the expression of CD80 and CD86 to 107% and 130%, respectively (FIGS. 4A and 4B). It was possible to observe such an effect even at lower concentrations (30 μM). In contrast, pre-incubation of rhsCD154 (100 ng/ml) with the other peptides, at the same concentration (60 μM), did not significantly affect the expression of CD80 and CD86 induced by stimulation with rhsCD154. At higher concentrations (250 μM) also peptides 4.6 (SEQ. ID NO: 3) and 4.11 (SEQ. ID NO: 7) showed inhibition of B cells activation: in particular, peptide 4.6 (SEQ. ID NO: 3) reduced the expression of CD80 at 117% and the expression of CD86 at 122%, whilst the effect of peptide 4.11 (SEQ. ID NO: 7) was not stably reproducible. In contrast, pre-incubation of rhsCD154 (100 ng/ml) with the control peptide 4.10-ala (SEQ. ID NO: 8), even at a concentration of 250 μM, neither affected the expression of CD80 and CD86 induced by stimulation with rhsCD154, nor it significantly reduced B cells activation, nor it reduced the expression levels of CD80 and CD86 (FIG. 4A). As the blocking control, rhsCD154 (100 ng/ml) was pre-incubated in all of the experiments carried out, prior to stimulation of B cells, with a blocking anti-human CD154 antibody (Alexis) for 15 minutes at 37° C., which completely inhibited CD40-mediated B cell activation and reduced the expression of CD80 and CD86 to basal levels (FIGS. 4A and 4B). The results are the mean±standard deviation of five different experiments. Similar results were also obtained with B cells isolated from human spleen fragments. Furthermore, in other experiments carried out on a naive B cell population, peptide 4.10 was shown to be effective to inhibit the CD40-mediated isotype switching of B cell Igs. These experiments were carried out on CD2T naive B cells, obtained from peripheral blood by negative selection, by depletion of mature lymphocytes from the B cell pool by immunomagnetic separation (MACS Systems Milteniy). The inventors demonstrated that when naive B cells are cultured for 96 hours in low glucose DMEM (Sigma) in the presence of IL-4 (0.4 ng/ml) and rhsCD154 (100 ng/ml), a significant increase (25%) in the number of B cells expressing membrane IgG was induced. In contrast, only a very low proportion of B cells stimulated with IL-4 (0.4 ng/ml) and rhsCD154 (100 ng/ml) in combination with peptide 4.10 (SEQ. ID NO: 6), underwent isotype switching (FIGS. 5A and 5B). Similarly, stimulation of naive B cells with IL-4 (0.4 ng/ml) and rhsCD154 (100 ng/ml) in combination with the blocking anti-human CD154 antibody did not induce isotype switching (FIGS. 5A and 5B).

It is known that an inflammatory process, once triggered, can be preserved by cells outside the immune system expressing particular receptors or lymphocyte co-stimulatory molecules, such as CD40 and its ligand CD154, such as e.g. endothelial cells from the vascular wall. Thus, the inventors demonstrated that peptide 4.10 (SEQ. ID NO: 6), besides inhibiting lymphocyte stimulation and/or maturation, is capable of limiting inflammation blocking the stimulation of the CD40 molecule expressed on the cell surface of endothelial cells. The inventors in fact demonstrated that the pro-angiogenic effect, evaluated in vitro both as single cell migration and as their ability to form vascular-like cell cords on basal matrix (Matrigel), induced by endothelial CD40 stimulation by administration of rhsCD154 (100 ng/ml), was inhibited by preincubating rhsCD154 (100 ng/ml) for 15 minutes at 37° C. with the anti-CD154 peptide 4.10 (SEQ. ID NO: 6) of the invention. In particular, the cell migration experiments were carried out with HUVEC cells plated on gelatin at a density of $4\times10^3$ in complete endothelial cell medium in the presence of 20% serum. The following day, the endothelial medium was replaced with low glucose DMEM (Sigma) with a reduced serum concentration (5%), in the presence or absence of rhsCD154 (100 ng/ml).

Furthermore, in order to evaluate the inhibitory effect, rhsCD154 (100 ng/ml) was pre-incubated for 15 minutes at 37° C. with peptide 4.10 (SEQ. ID NO: 6), or with control peptide 4.10-ala (SEQ. ID NO: 8), or with a blocking anti-human CD154 antibody. The flasks were then observed at 10× magnification for a period of 4 hours under a phase contrast inverted microscope equipped with a thermostatic chamber (at about 37° C.). The cells were photographed with a camera connected to the microscope, over the whole length of time of 4 hours at regular intervals of 15 minutes each. The migratory speed of each of the cells was calculated based on the position of the nucleus of each single cell in each single frame, using an image analysis software and, as a result, the average cell migratory speed (1 standard deviation) was calculated for each experimental condition. As shown in FIGS. 6A and 6B, stimulation of endothelial CD40 by rhsCD154 (100 ng/ml) induced an increase in the basal motility of cells (which was always lower than 12 μm/h) of about 350% (42 μm/h), whilst pre-incubation of rhsCD154 (100 ng/ml) for 15 minutes at 37° C. with peptide 4.10 (SEQ. ID NO: 6), as well as pre-incubation with the blocking anti-human CD154 antibody, drastically reduced the motility of the cells down to basal levels. In contrast, control peptide 4.10-ala (SEQ. ID NO: 8) did not affect endothelial CD40 stimulation (FIGS. 6A, 6B, 6C). As a further confirmation of the ability of peptide 4.10 to prevent human endothelial CD40 stimulation by rhsCD154 (100 ng/ml), HUVECs ($3.5\times10^4$) were subjected to an in vitro angiogenesis assay. HUVECs were plated on a tumor matrix (Matrigel, BD) capable of promoting the formation of super cellular organization, in a basal RPMI medium supplemented with 5% serum. Upon incubation at 37° C. under 5% $CO_2$ for 4 hours, the cells were observed under a contrast phase inverted microscope. FIGS. 7A and 7C show that stimulation with rhsCD154 (100 ng/ml) induced, after 4 hours already, the formation of a complex endothelial network, whilst pre-incubation of rhsCD154 (100 ng/ml) for 15 minutes at 37° C. with peptide 4.10 (SEQ. ID NO: 6), as well as with the blocking anti-human CD154 antibody, completely abrogated stimulation (FIGS. 7A, 7D and 7F). On the contrary, pre-incubation of rhsCD154 (100 ng/ml) for 15 minutes at 37° C. with control peptide 4.10-ala (SEQ. ID NO: 8), did not affect the ability of the cells to form vessel-like cell cords (FIG. 7E). The other anti-human CD154 peptides, such as 4.6 (SEQ. ID NO: 3) and 4.11 (SEQ. ID NO: 7), which do not specifically bind to the active site, were not capable of significantly reducing the stimulation of endothelial CD40 (data not shown).

Finally, the anti-angiogenic effect of peptide 4.10 was tested in an in vivo angiogenesis assay. Endothelial HUVEC cells ($2\times10^6$), resuspended in 200 μl of HANK'S solution, were mixed with 500 μl of Matrigel in liquid form containing rhsCD154 (100 ng/ml), and inoculated subcutaneously into SCID mice in the right and left side of the hip, in the presence and in the absence of peptide 4.10 (SEQ. ID NO: 6), respectively. After 6 days, the mice were killed and the Matrigel plugs were recovered and fixed in 10% formalin solution for at least 24 hours, then processed for immunohystochemical analysis. Hematoxylin-eosin stained histological sections of HUVEC and rhsCD154 grafts showed strong angiogenesis (FIGS. 8A and 8B), which was significantly inhibited or completely absent in inocula in which sCD154 was pre-incubated with peptide 4.10 (SEQ. ID NO: 6), where the majority of cells had undergone apoptosis (FIGS. 8A and 8C).

Peptide 4.10 (SEQ ID NO: 6) also proved to be capable of inhibiting CLL tumor cell survival obtained in vivo by cultivation in the presence of IL-4. Resistance to apoptosis and enhanced survival of the CLL cells is believed responsible of the in vivo expansion of these tumor cells in Chronic Lymphocytic Leukemia patients. These results indicate that the interaction between CD40 and its ligand CD154 is important for stimulating CLL cells survival and that inhibition of the CD40:CD154 interaction with a peptide which is capable of recognizing the active site of CD154 may inhibit survival of these cells (FIG. 9).

Finally, one of the major advantages of peptide 4.10 is its lack of reactivity towards human platelets. It is know that in the past, a number of clinical trials carried out to test promising anti-CD154 monoclonal antibodies were suddenly discontinued due to dramatic prothrombotic side effects (Kelsoe G. et al, J. Clin. Invest. 2003). The hypothesis is that the anti-CD154 antibodies had triggered a cross-reaction on the surface of human platelets expressing the receptor for the Fc immunoglobulin fraction (FcR) and, after activation, the CD154 molecule. Thus, the inventors tested the effect of peptide 4.10 on platelets, by a platelet aggregation assay. Such experiments were carried out by the use of a thermostatic aggregometer, equipped with a magnetic stirrer and a real time optical density meter. Platelet aggregation was evaluated as the change in optical density versus the reference sample (blank). The experiments were carried out on platelets extracted from peripheral whole blood of healthy donors collected in tubes containing 5 U/ml heparin. In particular, the platelet enriched plasma (PRP), was obtained by whole blood centrifugation at 900 rpm for 20 minutes, while the platelet poor plasma (PPP), used as the reference sample, was obtained collecting the supernatant after another centrifugation at 3000 rpm for 10 minutes. As previously demonstrated by Langer (Langer F. et al, Thromb. Haemost. 2005), priming the platelets by incubation for 10 minutes at 37° C. with immunocomplexes consisting of recombinant human soluble CD154 and the anti-CD154 monoclonal antibody enhanced platelet aggregation induced by subsequent stimulation with ADP 0.5 µM (FIG. 10). On the contrary, priming with CD154 alone or in combination with peptide 4.10 (60 µM) did not enhance platelet aggregation induced by stimulation with ADP 0.5 µM (FIG. 10). Similar results were obtained inducing platelet aggregation with 0.3 U/ml thrombin.

Since endothelial cells frequently express CD40 on their surface, especially at the site of inflammation, and since angiogenesis may play a major role in the development of several inflammatory processes and diseases, the above-illustrated properties of the 4.10 peptide of the invention render such a peptide a very promising molecule for the development of potential anti-inflammatory approaches. Furthermore, the inhibiting effect exerted by the 4.10 peptide (SEQ ID NO: 6) on lymphocyte activation, provides a potential use of this molecule as an immunosuppressive therapy directed to transplantation or to tumor diseases in which tumor cell proliferation is supported by the anti-apoptotic effect resulting from the stimulation of CD40, such as for example in Chronic Lymphocytic Leukemia (CLL).

TABLE I

| Clone | Sequence | SEQ ID NO: |
|---|---|---|
| 4.1 | — | — |
| 4.2 = 4.3 | CPSGHTKAC | 1 |
| 4.4 | CGTHSSRIC | 2 |
| 4.5 | — | — |
| 4.6 | CLGTQNKEC | 3 |
| 4.7 = 4.12 | CTPGKPHSC | 4 |
| 4.8 | CKAASANIC | 5 |
| 4.9 | — | — |
| 4.10 | CLPTRHMAC(*) | 6 |
| 4.11 | CLSAVHNMC | 7 |

(*)peptide according to the invention

TABLE II

| Clone | Sequence | SEQ ID NO: |
|---|---|---|
| 4.10-ala | CLPTAHMAC | 8 |
| 4.101 | CIPTRHMAC | 9 |
| 4.102 | CLPSRHMAC | 10 |
| 4.103 | CIPTRHMVC | 11 |
| 4.104 | CLPTRWMAC | 12 |

REFERENCES 1. van Kooten, C., and J. Banchereau. 2000. CD40-CD40 ligand. J. Leukoc. Biol. 67: 2-17.
2. Aruffo, A., M. Farrington, D. Hollenbaugh, X. Li, A. Milatovich, S, Nonoyama, J. Bajorath, L. S. Grosmaire, R. Stenkamp, M. Neubauer, et al. 1993. The CD40 ligand, gp39, is defective in activated T cells from patients with X-linked hyper-IgM syndrome. Cell. 72: 291-300.
3. Schonbeck, U., and P. Libby. 2001. CD40 signaling and plaque instability. Circ. Res. 89: 1092-1103.
4. Heim, V., J. R. Slupsky, M. Grafe, I. Anagnostopoulos, R. Forster, G. Muller-Berghaus, and R. A. Kroczek. 1998. CD40 ligand on activated platelets triggers an inflammatory reaction of endothelial cells. Nature. 391: 591-594.
5. Biancone, L., V. Cantaluppi, and G. Camussi. 1999. CD40-CD154 interaction in experimental and human disease. Int. J. Mol. Med. 3: 343-353.
6. Buchner, K., V. Henn, M. Grafe, O. J. de Boer, A. E. Becker, and R. A. Kroczek. 2003. CD40 ligand is selectively expressed on CD4+ T cells and platelets: implications for CD40-CD40L signalling in atherosclerosis. J. Pathol. 201: 288-295.
7. Bussolati, B., S. Russo, I. Deambrosis, V. Cantaluppi, A. Volpe, U. Ferrando, and G. Camussi. 2002. Expression of CD154 on renal cell carcinomas and effect on cell proliferation, motility and platelet-activating factor synthesis. Int. J. Cancer. 100: 654-661.
8. Biancone, L., V. Cantaluppi, M. Boccellino, L. Del Sorbo, S. Russo, A. Albini, I. Stamenkovic, and G. Camussi. 1999. Activation of CD40 favors the growth and vascularization of Kaposi's sarcoma. J. Immunol. 163: 6201-6208.
9. Cantaluppi, V., M. C. Deregibus, L. Biancone, I. Deambrosis, B. Bussolati, A. Albini, and G. Camussi. 2006. The expression of CD154 by Kaposi's sarcoma cells mediates the anti-apoptotic and migratory effects of HIV-1-TAT protein. Int. J. Immunopathol. Pharmacol. 19: 81-96.

10. Hill, S. C., S. J. Youde, S. Man, G. R. Teale, A. J. Baxendale, A. Hislop, C. C. Davies, D. M. Luesley, A. M. Blom, A. B. Rickinson, L. S. Young, and A. G. Eliopoulos. 2005. Activation of CD40 in cervical carcinoma cells facilitates CTL responses and augments chemotherapy-induced apoptosis. J. Immunol. 174: 41-50.
11. Melichar, B., R. Patenia, S. Gallardo, K. Melicharova, W. Hu, and R. S. Freedman. 2007. Expression of CD40 and growth-inhibitory activity of CD40 ligand in ovarian cancer cell lines. Gynecol. Oncol. 104: 707-713.
12. Eliopoulos, A. G., and L. S. Young. The role of the CD40 pathway in the pathogenesis and treatment of cancer. 2004. Curr. Opin. Pharmacol. 4: 360-367-13. Dicker F., Kater A. P., Prada C. E., Fukuda T., and Kipps T. J. 2006. CD154 induces p73 to overcome the resistance to apoptosis of chronic lymphocytic leukemia cells lacking functional p53. Blood. 108: 450-3457.
14. Boumpas, D. T., R. Furie, S. Manzi, G. G. Illei, D. J. Wallace, J. E. Balow, and A. Waishnaw. 2003. A short course of BG 9588 (anti CD40 ligand antibody) improves serologic activity and decreases hematuria in patients with proliferative lupus glomerulonephritis. Arthritis Rheum. 46: 3251-3258.
15. Liossis, S. N., and P. P. Sfikakis. 2004. Costimulation blockade in the treatment of rheumatic diseases. BioDrugs. 18: 95-102.
16. Daoussis, D., A. P. Andonopoulos, S. N. Liossis. 2004. Targeting CD40L: a promising therapeutic approach. Clin. Diagn. Lab. Immunol. 11: 635-641.
17. Molano, R. D., T. Berney, H. Li, P. Cattan, A. Pileggi, C. Vizzardelli, N. S. Kenyon, C. Ricordi, L. C. Burkly, and L. Inverardi. 2001. Prolonged islet graft survival in NOD mice by blockade of the CD40-CD154 pathway of T-cell costimulation. Diabetes. 2001. 50: 270-276.
18. Quezada, S. A., B. Fuller, L. Z. Jarvinen, M. Gonzalez, B. R. Blazar, A. Y. Rudensky, T. B. Strom, and R. J. Noelle. 2003. Mechanisms of donor-specific transfusion tolerance: preempitive induction of clonal T-cell exhaustion via indirect presentation. Blood. 102: 1920-1926.
19. Elster, E. A., D. A. Hale, R. B. Mannon, L. C. Cendales, S. J. Swanson, and A. D. Kirk. 2004. The road to tolerance: renal transplant tolerance induction in nonhuman primate studies and clinical trials. Transpl. Immunol. 13: 87-99.
20. Xu, H., X. Zhang, R. B. Mannon, and A. D. Kirk. 2006. Platelet-derived or soluble CD154 induces vascularized allograft rejection independent of cell-bound CD154. J. Clin. Invest. 116: 769-774.
21. Snanoudj, R., H. de Preneuf, C. Creput, N. Arzouk, B. Deroure, S. Beaudreuil, A. Durrbach, and B. Charpentier. 2006. Costimulation blockade and its possible future use in clinical transplantation. Transpl. Int. 19: 693-704.
22. Nanji, S. A., W. W. Hancock, B. Luo, C. D. Schur, R. L. Pawlick, L. F. Zhu, C. C. Anderson, and A. M. Shapiro. 2006. Costimulation blockade of both inducible costimulator and CD40 ligand induces dominant tolerance to islet allografts and prevents spontaneous autoimmune diabetes in the NOD mouse. Diabetes. 55: 27-33.
23. Allen, S. D., S. V. Rawale, C. C. Whitacre, and P. T. P. Kaumaya. 2005. Therapeutic peptidomimetic strategies for autoimmune diseases: costimulation blockade. J. Peptide Res. 65: 591-604.
24. Ladner, R. C., A. K. Sato, J. Gorzelany and M. de Souza. 2004. Phage display-derived peptides as therapeutic alternatives to antibodies. DDT. 12:525-529.
25. Hetian, L., A. Ping, S. Shumei, L. Xiaoying, H. Luowen, W. Jian, M. Lin, L. Meisheng, Y. Junshan and S. Chengchao. 2002. A novel peptide isolated from phage display library inhibits tumor growth and metastasis by blocking the binding of vascular endothelial growth factor to its kinase domain receptor. J. Biol. Chem. 277: 43137-43142.
26. Kelsoe, G. 2003. Therapeutic CD154 antibody for lupus: promise for the future? J. Clin. Invest. 112: 1480-1482.
27. Langer, F., S. B. Ingersoll, A. Amirkhosravi, T. Meyer, F. A. Siddiqui, S. Ahmad, J. M. Walker, M. Amaya, H., Desai, J. L. Francis. 2005. The role of CD40 in CD40L- and antibody-mediated platelet activation. Thromb. Haemost. 93:1137-1146.

The invention claimed is:

1. A peptide capable of selectively binding to the active site of the CD154 receptor and capable of inhibiting CD40:CD154 interaction, comprising the CD154-binding hepta-amino acid sequence SEQ ID NO: 13.

2. The peptide according to claim 1, which is from 7 to 30 amino acids in length.

3. The peptide according to claim 1, wherein the CD154-binding amino acid sequence SEQ ID NO: 13 has a flanking cysteine at each end of the sequence, thereby providing nona-amino acid sequence SEQ ID NO: 6.

4. The peptide according to claim 3, consisting of amino acid sequence SEQ ID NO: 6.

5. The peptide according to claim 3, which is in a cyclic form.

6. A multimeric structure comprising a plurality of copies of the peptide according to claim 1.

7. The multimeric structure according to claim 6, wherein each of the copies of the peptide is either in a linear form or in a cyclic form.

8. The multimeric structure according to claim 6, wherein each of the copies of the peptide is linked to at least one other copy by at least one amino acid spacer.

9. The multimeric structure according to claim 8, wherein the amino acid spacer is a Gly (G) residue.

10. The multimeric structure according to claim 8, comprising an amino acid core to which each of the copies of the peptide is directly or indirectly linked.

11. The multimeric structure according to claim 10, wherein the amino acid core consists of a plurality of Lys (K) residues.

12. The multimeric structure according to claim 6, wherein each of the plurality of copies of the peptide consists of the hepta-amino acid sequence SEQ ID NO: 13 in a linear form.

13. The multimeric structure according to claim 12 consisting of the following structure:

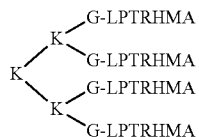

wherein L is Leu, P is Pro, T is Thr, R is Arg, H is His, M is Met, A is Ala, G is Gly and K is Lys.

14. A conjugate comprising at least one peptide according to claim 1 or at least one multimeric structure having a plurality of copies of the peptide according to claim 1, conjugated to a molecule selected from the group consisting of biomolecules, diagnostic agents and therapeutic agents.

15. The conjugate according to claim 14, wherein the therapeutic agent is an anti-inflammatory, immunosuppressive, immunomodulatory or anti-tumor agent.

16. The conjugate according to claim 14, wherein the therapeutic agent is capable of exerting a cytotoxic effect on activated endothelial cells, tumor cells or cells expressing CD154 at their surface upon activation.

17. The conjugate according to claim 14, wherein the diagnostic agent is an in vivo detectable molecule.

18. The conjugate according to claim 14, wherein the diagnostic agent is a detectable molecule for an in vitro assay.

19. The peptide according to claim 1 or a multimeric structure having a plurality of copies of the peptide according to claim 1, as a medicament.

20. A pharmaceutical composition comprising an effective amount of a peptide according to claim 1 or a multimeric structure having a plurality of copies of the peptide according to claim 1, and a pharmaceutically acceptable vehicle and/or excipient.

* * * * *

UNITED STATES PATENT AND TRADEMARK OFFICE
CERTIFICATE OF CORRECTION

PATENT NO.       : 8,507,448 B2                                                    Page 1 of 1
APPLICATION NO. : 12/734908
DATED            : August 13, 2013
INVENTOR(S)      : Camussi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 332 days.

Signed and Sealed this

Fifteenth Day of September, 2015

Michelle K. Lee
*Director of the United States Patent and Trademark Office*

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: binding protein

<400> SEQUENCE: 1

Cys Pro Ser Gly His Thr Lys Ala Cys
1               5

<210> SEQ ID NO 2
<211> LENGTH: 9
<212> TYPE: PRT
<213> ORGANISM: Artificial Sequence
<220> FEATURE:
<223> OTHER INFORMATION: binding protein

<400> SEQUENCE: 2

Cys Gly Thr His Ser Ser Arg Ile Cys
1               5
```

```
<210> SEQ ID NO 3
<211> LENGTH: 9
<212> TYPE: PRT
<213> ORGANISM: Artificial Sequence
<220> FEATURE:
<223> OTHER INFORMATION: binding protein

<400> SEQUENCE: 3

Cys Leu Gly Thr Gln Asn Lys Glu Cys
1               5

<210> SEQ ID NO 4
<211> LENGTH: 9
<212> TYPE: PRT
<213> ORGANISM: Artificial Sequence
<220> FEATURE:
<223> OTHER INFORMATION: binding protein

<400> SEQUENCE: 4

Cys Thr Pro Gly Lys Pro His Ser Cys
1               5

<210> SEQ ID NO 5
<211> LENGTH: 9
<212> TYPE: PRT
<213> ORGANISM: Artificial Sequence
<220> FEATURE:
<223> OTHER INFORMATION: binding protein

<400> SEQUENCE: 5

Cys Lys Ala Ala Ser Ala Asn Ile Cys
1               5

<210> SEQ ID NO 6
<211> LENGTH: 9
<212> TYPE: PRT
<213> ORGANISM: Artificial Sequence
<220> FEATURE:
<223> OTHER INFORMATION: binding protein

<400> SEQUENCE: 6

Cys Leu Pro Thr Arg His Met Ala Cys
1               5

<210> SEQ ID NO 7
<211> LENGTH: 9
<212> TYPE: PRT
<213> ORGANISM: Artificial Sequence
<220> FEATURE:
<223> OTHER INFORMATION: binding protein

<400> SEQUENCE: 7

Cys Leu Ser Ala Val His Asn Met Cys
1               5

<210> SEQ ID NO 8
<211> LENGTH: 9
<212> TYPE: PRT
<213> ORGANISM: Artificial Sequence
<220> FEATURE:
<223> OTHER INFORMATION: binding protein

<400> SEQUENCE: 8

Cys Leu Pro Thr Ala His Met Ala Cys
1               5

<210> SEQ ID NO 9
```

```
<211> LENGTH: 9
<212> TYPE: PRT
<213> ORGANISM: Artificial Sequence
<220> FEATURE:
<223> OTHER INFORMATION: binding protein

<400> SEQUENCE: 9

Cys Ile Pro Thr Arg His Met Ala Cys
1               5

<210> SEQ ID NO 10
<211> LENGTH: 9
<212> TYPE: PRT
<213> ORGANISM: Artificial Sequence
<220> FEATURE:
<223> OTHER INFORMATION: binding protein

<400> SEQUENCE: 10

Cys Leu Pro Ser Arg His Met Ala Cys
1               5

<210> SEQ ID NO 11
<211> LENGTH: 9
<212> TYPE: PRT
<213> ORGANISM: Artificial Sequence
<220> FEATURE:
<223> OTHER INFORMATION: binding protein

<400> SEQUENCE: 11

Cys Ile Pro Thr Arg His Met Val Cys
1               5

<210> SEQ ID NO 12
<211> LENGTH: 9
<212> TYPE: PRT
<213> ORGANISM: Artificial Sequence
<220> FEATURE:
<223> OTHER INFORMATION: binding protein

<400> SEQUENCE: 12

Cys Leu Pro Thr Arg Trp Met Ala Cys
1               5

<210> SEQ ID NO 13
<211> LENGTH: 7
<212> TYPE: PRT
<213> ORGANISM: Artificial Sequence
<220> FEATURE:
<223> OTHER INFORMATION: binding protein

<400> SEQUENCE: 13

Leu Pro Thr Arg His Met Ala
1               5
```